US00PP19666P2

(12) United States Plant Patent
Wain

(10) Patent No.: US PP19,666 P2
(45) Date of Patent: Feb. 3, 2009

(54) ***CHRYSANTHEMUM* PLANT NAMED 'YOGIGI PINK'**

(50) Latin Name: *Chrysanthemum×morifolium*
Varietal Denomination: Yogigi Pink

(76) Inventor: Peter Wain, Southampton (GB)

( * ) Notice: Subject to any disclaimer, the term of this patent is extended or adjusted under 35 U.S.C. 154(b) by 0 days.

(21) Appl. No.: 12/006,787

(22) Filed: Jan. 3, 2008

(51) Int. Cl.
*A01H 5/00* (2006.01)

(52) U.S. Cl. ..... Plt./291

(58) Field of Classification Search ..... Plt./291
See application file for complete search history.

*Primary Examiner*—Annette H Para
*Assistant Examiner*—S. B. McCormick-Ewoldt

(57) ABSTRACT

A new and distinct cultivar of *Chrysanthemum* plant named 'Yogigi Pink', characterized by its compact, upright, outwardly spreading and rounded plant habit; freely branching habit; dense and full plant habit; uniform and freely flowering habit; decorative-type inflorescences with obovate-shaped ray florets; two-toned ray florets that are initially dark pink in color becoming lighter pink with development; and natural season flowering about September 26$^{th}$ in the Northern Hemisphere.

1 Drawing Sheet

Botanical designation: *Chrysanthemum×morifolium.*
Cultivar denomination: 'Yogigi Pink'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yogigi Pink'.

The new *Chrysanthemum* is a naturally-occurring whole plant mutation of the *Chrysanthemum×morifolium* cultivar Yogigi, not patented. The new *Chrysanthemum* was discovered and selected by the Inventor as a single flowering plant from within a population of plants of the cultivar Yogigi in a controlled environment in Alva, Fla. in May, 2005.

Asexual reproduction of the new *Chrysanthemum* by vegetative cuttings was first conducted in Alva, Fla. in July, 2005. Asexual reproduction by cuttings has shown that the unique features of this new *Chrysanthemum* are stable and reproduced true to type in successive generations.

SUMMARY OF THE INVENTION

Plants of the cultivar Yogigi Pink have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yogigi Pink'. These characteristics in combination distinguish 'Yogigi Pink' as a new and distinct garden *Chrysanthemum* cultivar:

1. Compact, upright, outwardly spreading and rounded plant habit.
2. Freely branching habit; dense and full plant habit.
3. Uniform and freely flowering habit.
4. Decorative-type inflorescences with obovate-shaped ray florets.

5. Two-toned ray florets that are initially dark pink in color becoming lighter pink with development.
6. Natural season flowering about September 26$^{th}$ in the Northern Hemisphere.

In side-by-side comparisons conducted in Alva, Fla., plants of the new *Chrysanthemum* differed from plants of the parent, the cultivar Yogigi, in the following characteristics:

1. Plants of the new *Chrysanthemum* and the cultivar Yogigi differ in ray floret color as plants of the cultivar Yogigi have lighter and less intense pink-colored ray florets.
2. Ray florets of plants of the new *Chrysanthemum* resist fading better than ray florets of teh cultivar Yogigi.

Plants of the new *Chrysanthemum* can be compared to plants of the *Chrysanthemum* cultivar Lynn, disclosed in U.S. Plant Pat. No. 8,171. In side-by-side comparisons conducted in Alva, Fla., plants of the new *Chrysanthemum* differed from plants of the cultivar Lynn in the following characteristics:

1. Plants of the new *Chrysanthemum* were smaller and more rounded than plants of the cultivar Lynn.
2. Plants of the new *Chrysanthemum* were more flexible and less brittle than plants of the cultivar Lynn.
3. Plants of the new *Chrysanthemum* had smaller inflorescences than plants of the cultivar Lynn.

BRIEF DESCRIPTION OF THE PHOTOGRAPHS

The accompanying photographs illustrate the overall appearance of the new *Chrysanthemum.* The photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Yogigi Pink'.

The photograph at the top of the sheet is a close-up view of typical inflorescences of 'Yogigi Pink'.

DETAILED BOTANICAL DESCRIPTION

The aforementioned photographs and following observations and measurements describe plants grown in Monroeville, N.J. during the late summer and autumn in an outdoor nursery and under conditions and practices which approximate those generally used in commercial garden *Chrysanthemum* production. During the production of the plants, day temperatures averaged 29° C. and night temperatures averaged 18° C. Plants were grown in containers under natural daylength. Plants used in the photographs and for the description were not pinched and were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yogigi Pink.

Parentage: Naturally-occurring whole plant mutation of the *Chrysanthemum×morifolium* cultivar Yogigi, not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum.* Compact, stems upright and outwardly spreading giving a uniformly rounded appearance to the plant. Freely branching habit, about 15 lateral branches develop after removal of teminal apex (pinching) each with numerous secondary laterals; dense and full plant habit. Moderately vigorous growth habit.

*Plant height.*—About 23 cm.

*Plant width.*—About 51 cm.

*Lateral branches.*—Length: About 26 cm. Diameter: About 6 mm. Internode length: About 1.5 cm. Strength: Strong, flexible. Texture: Pubescent. Color: Close to 147C.

*Leaves.*—Arrangement: Alternate, simple. Length: About 3 cm. Width: About 2.4 cm. Shape: Palmately-lobed; roughly ovate. Apex: Acute. Base: Attenuate. Margin: Palmately lobed, sinuses between lateral lobes parallel to divergent. Texture, upper and lower surfaces: Fine pubescence; veins prominent on lower surface. Color: Developing and fully expanded foliage, upper surface: 137A; venation, 146B. Developing and fully expanded foliage, lower surface: 137B; venation, 147C. Petiole: Length: About 8 mm. Diameter: About 3 mm. Texture, upper and lower surfaces: Pubescent. Color, upper and lower surfaces: 147C.

Inflorescence description:

*Appearance.*—Decorative-type inflorescence form with obovate-shaped ray florets. Inflorescences borne on terminals above foliage. Disc and ray florets arranged acropetally on a capitulum. Inflorescences fragrant; pungent, herbaceous.

*Flowering response.*—Under natural season conditions, plants flower about September 26$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 45 days later.

*Postproduction longevity.*—Plants maintain good color and substance for about four weeks.

*Quantity of inflorescences.*—About 64 inflorescences develop per lateral branch.

*Inflorescence bud.*—Height: About 8 mm. Diameter: About 1.2 cm. Shape: Oblate. Color: Close to 75A to 75B.

*Inflorescence size.*—Diameter: About 3.5 cm. Depth (height): About 1.3 cm. Disc diameter: About 5 mm. Receptacle diameter: About 1.4 cm. Receptacle height: About 3 mm. Receptacle color: 148A.

*Ray florets.*—Orientation: Initially upright, then about 90° from vertical or perpendicular to peduncle. Length: About 1.5 cm. Width: About 6 mm. Shape: Obovate. Apex: Acute to emarginate. Base: Acute. Margin: Entire. Texture, upper and lower surfaces: Smooth, glabrous, velvety. Number of ray florets per inflorescence: About 220 arranged in about ten whorls. Color: When opening, upper surface: Close to 155D; towards the margins tinted with close to 78A to 78D. When opening, lower surface: Close to 155D; towards the margins, tinted with close to 78C. Fully opened, upper surface: Close to 155D tinted with close to 75C to 75D. Fully opened, lower surface: Close to 155D tinted with close to 75A.

*Disc florets.*—Shape: Tubular, elongated. Length: About 6 mm. Diameter: About 1 mm. Number of disc florets per inflorescence: About 16. Color, immature: Apex: Close to 13A. Mid-section: Close to 1C. Base: Close to 157A. Color, mature: Apex: Close to 14A. Mid-section: Close to 1C. Base: Close to 157A.

*Phyllaries.*—Number of phyllaries per inflorescence: About 20 arranged in about three whorls. Length: About 7 mm. Width: About 3 mm. Shape: Elliptical. Apex: Acute. Base: Truncate. Texture, upper surface: Smooth, waxy. Texture, lower surface: Pubescent. Color, upper surface: Close to 144A. Color, lower surface: Close to 146C.

*Peduncles.*—Length, terminal peduncle: About 5.8 cm. Length, fourth peduncle: About 9.6 cm. Diameter, terminal peduncle: About 2 mm. Angle: About 30° to 45° from vertical. Strength: Strong; flexible. Texture: Pubescent; longitudinally ridged. Color: Close to 147C.

*Reproductive organs.*—Androecium: Stamen number: About five per floret. Filament length: About 2 mm. Filament color: Close to 157D. Anther length: About 1 mm. Anther shape: Narrowly lanceolate. Anther color: Close to 15A. Pollen amount: Scarce. Pollen color: Close to 15A. Gynoecium: Pistil length: About 6 mm. Stigma shape: Bi-parted. Stigma color: Close to 12B. Style length: About 3 mm. Style color: Close to 145B. Ovary color: Close to 157C.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yogigi Pink' as illustrated and described.

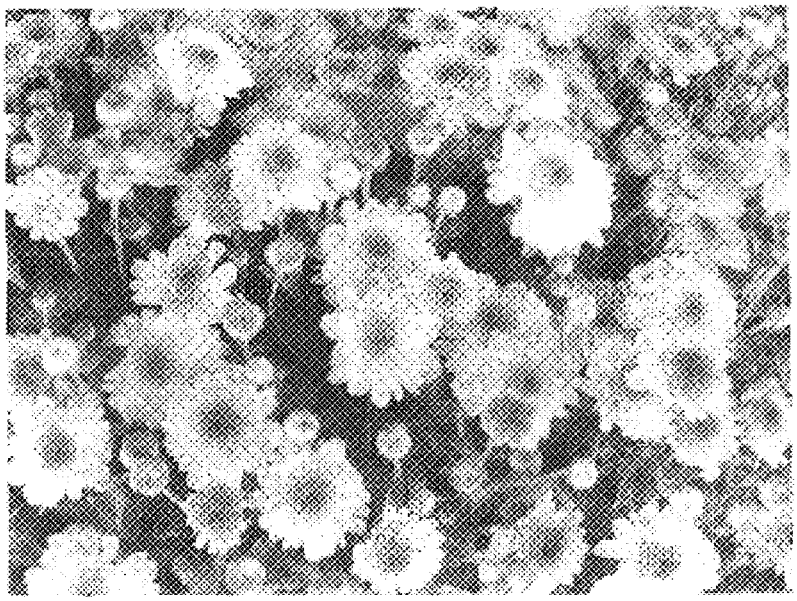
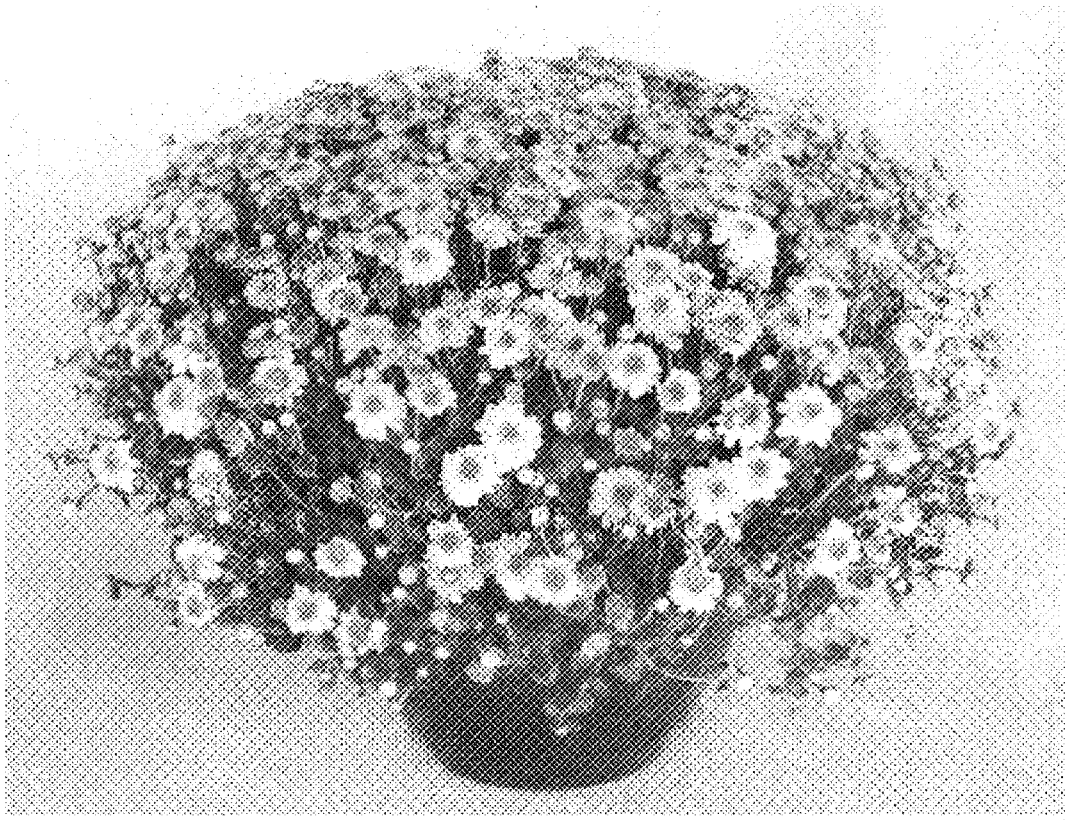

* * * * *